United States Patent [19]

Munch

[11] 3,980,892
[45] Sept. 14, 1976

[54] SKULL CLAMP, MAINLY FOR X-RAY APPARATUS

[75] Inventor: Jozef Munch, Edegem, Belgium

[73] Assignee: C. G. R. -Benelux N.V.

[22] Filed: Aug. 18, 1975

[21] Appl. No.: 605,659

Related U.S. Application Data

[63] Continuation of Ser. No. 301,353, Oct. 27, 1972, abandoned.

[30] Foreign Application Priority Data

Oct. 28, 1971 Belgium .......................... 51413/71

[52] U.S. Cl. ............................... 250/456; 250/451
[51] Int. Cl.² ...................................... G01M 23/00
[58] Field of Search ........... 250/439, 440, 442, 451, 250/456

[56] References Cited
UNITED STATES PATENTS

| 1,688,382 | 10/1928 | Ghrist | 250/456 |
| 1,747,434 | 2/1930 | Ghrist | 250/456 |
| 1,857,503 | 5/1932 | Ghrist | 250/456 |
| 3,025,397 | 3/1962 | Travis et al. | 250/456 |

*Primary Examiner*—Alfred E Smith
*Assistant Examiner*—B. C. Anderson
*Attorney, Agent, or Firm*—Ulle C. Linton

[57] ABSTRACT

A device for supporting the skull of a person laying horizontally, mainly for taking X-ray photographs of the skull and which device is adjustable for bringing the skull to a desired position and retaining the skull while being X-rayed.

8 Claims, 5 Drawing Figures

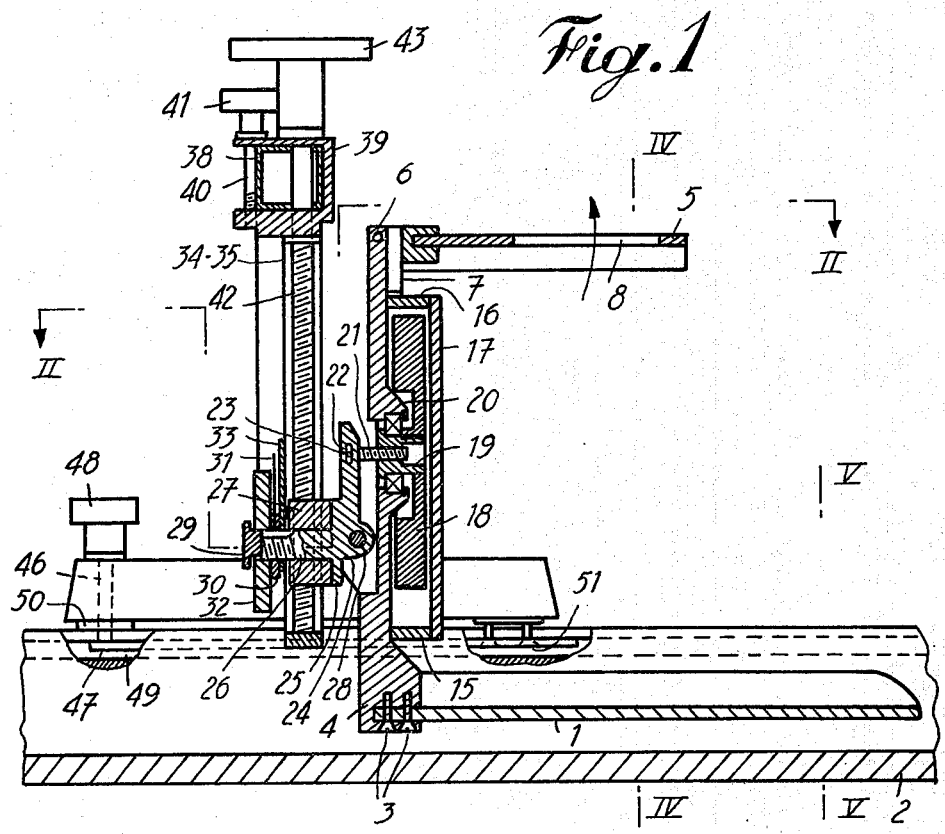
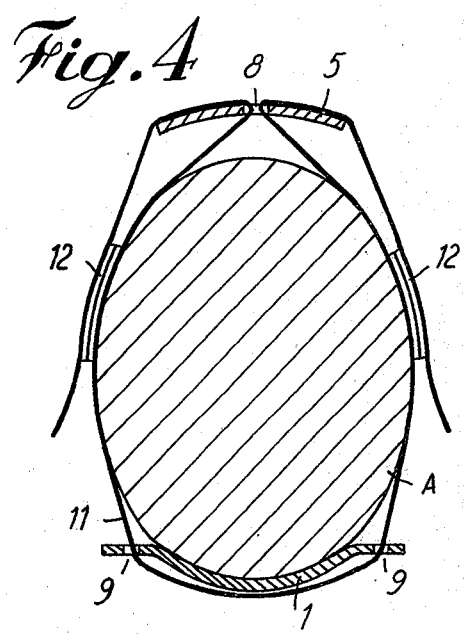
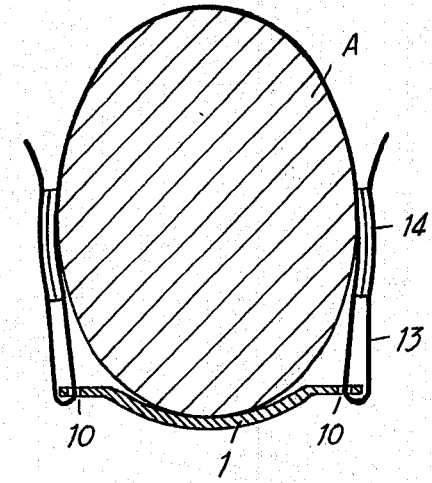

SKULL CLAMP, MAINLY FOR X-RAY APPARATUS

This is a continuation of application Ser. No. 301,353, filed Oct. 27, 1972 now abandoned.

The invention concerns a device for clamping a skull and bringing it into a required position, such a device being mainly usefull when making X-ray photographs.

For this purpose a skull clamp is known which consists chiefly of a support which is fixed, for instance by means of suction disks, on the bed of an X-ray apparatus, said support having an upright column along which two arms which are hinged in a horizontal plane can be displaced in height, the free end of each of these arms being provided with a longitudinally slidable pressure pad, between which the skull is clamped. Aforesaid arms can also be rotated in a vertical plane with respect to the column.

This sort of clamp does however have the disadvantages that a skull can never be clamped to complete immobility and that a feeling of pain is experienced when the pressure pads are clamped against the skull. Moreover, due to the hinged arms located on both sides of the skull, the latter is no longer accessible at all essential locations required for carrying out certain skull measurements or for making X-ray photographs. It is moreover not possible with this type of skull clamp to place the skull in all essential positions.

In order to eliminate these inconveniences, a skull clamp according to the present invention was made, by means of which it is possible painlessly to clamp a skull and hold it motionless whilst maintaining a maximum accessibility all around the skull for carrying out all sorts of required operations, such as measurements or the taking of X-ray photographs. This clamp moreover offers the advantage that the skull can be displaced into all essential positions.

For this purpose and according to the present invention, the skull clamp consists mainly of a carrier plate out of some material which is permeable to X-rays and upon which the to be radiographed skull rests, of means for binding the skull motionless upon aforesaid carrier plate, of a bridge fitted transversally across the bed of the X-ray apparatus and which can be moved longitudinally along aforesaid bed, from which bridge the carrier plate is suspended by a means which permits the lateral displacement of the carrier plate with respect to the bridge, of some means for adjusting the height of the carrier plate, of a means for adjusting the carrier plate transversally to the required angle, and of a means for adjusting the carrier plate longitudinally to the required angle.

Merely as an example and without the slightest intent of limitation, a more detailed description will be given below of a chosen, but in no way restricted form of embodiment of a skull clamp according to the present invention. This description refers to the appended drawings in which:

FIG. 1 represents a longitudinal section with other partial sections of the skull clamp;

FIGS. 4 and 5 represent cross sections with fitted straps, and such respectively according to lines IV—IV and V—V of FIG. 1.

Figure 2:
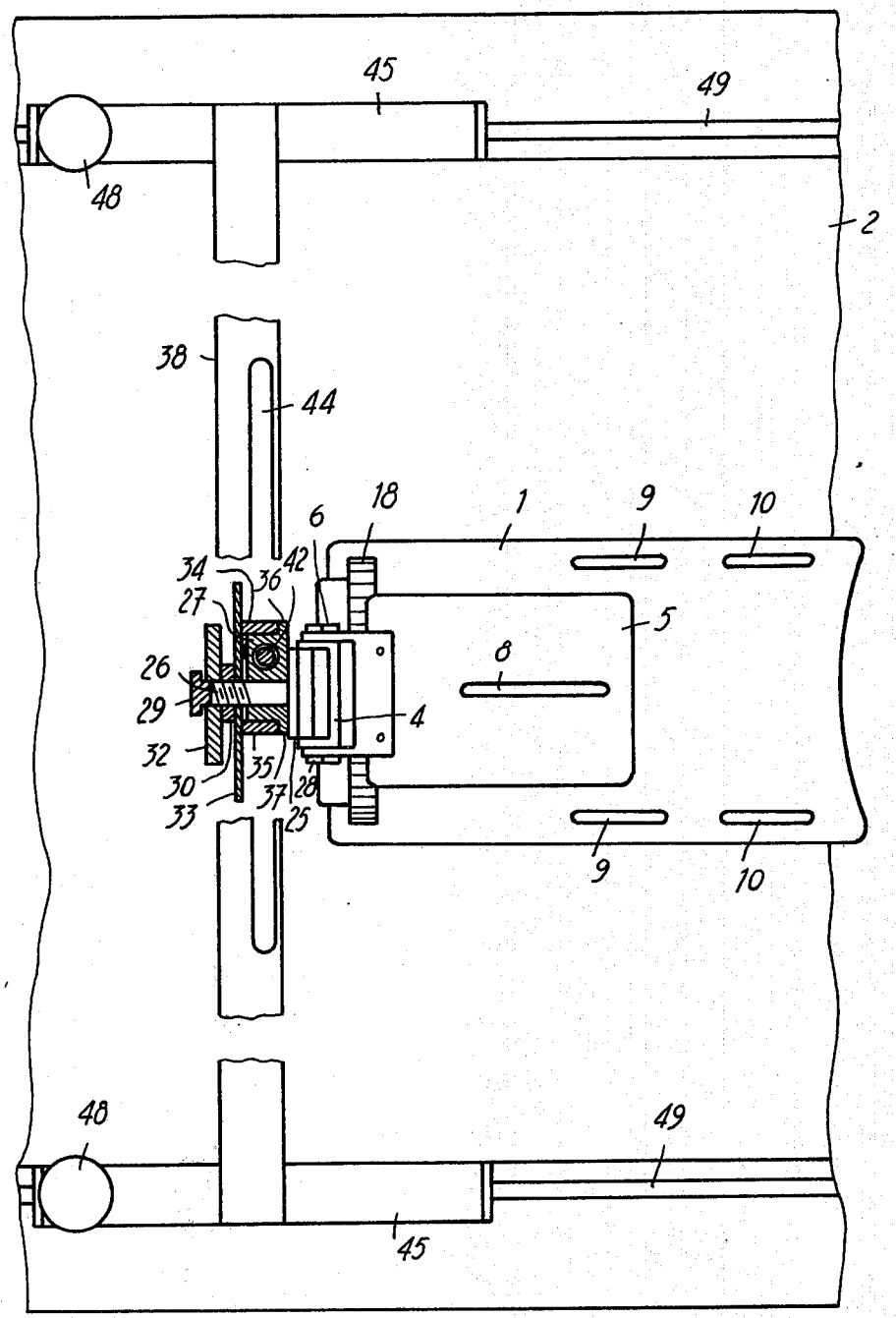
FIG. 2 shows a top view thereof with partial sections according to line II—II from FIG. 1.
Figure 3:
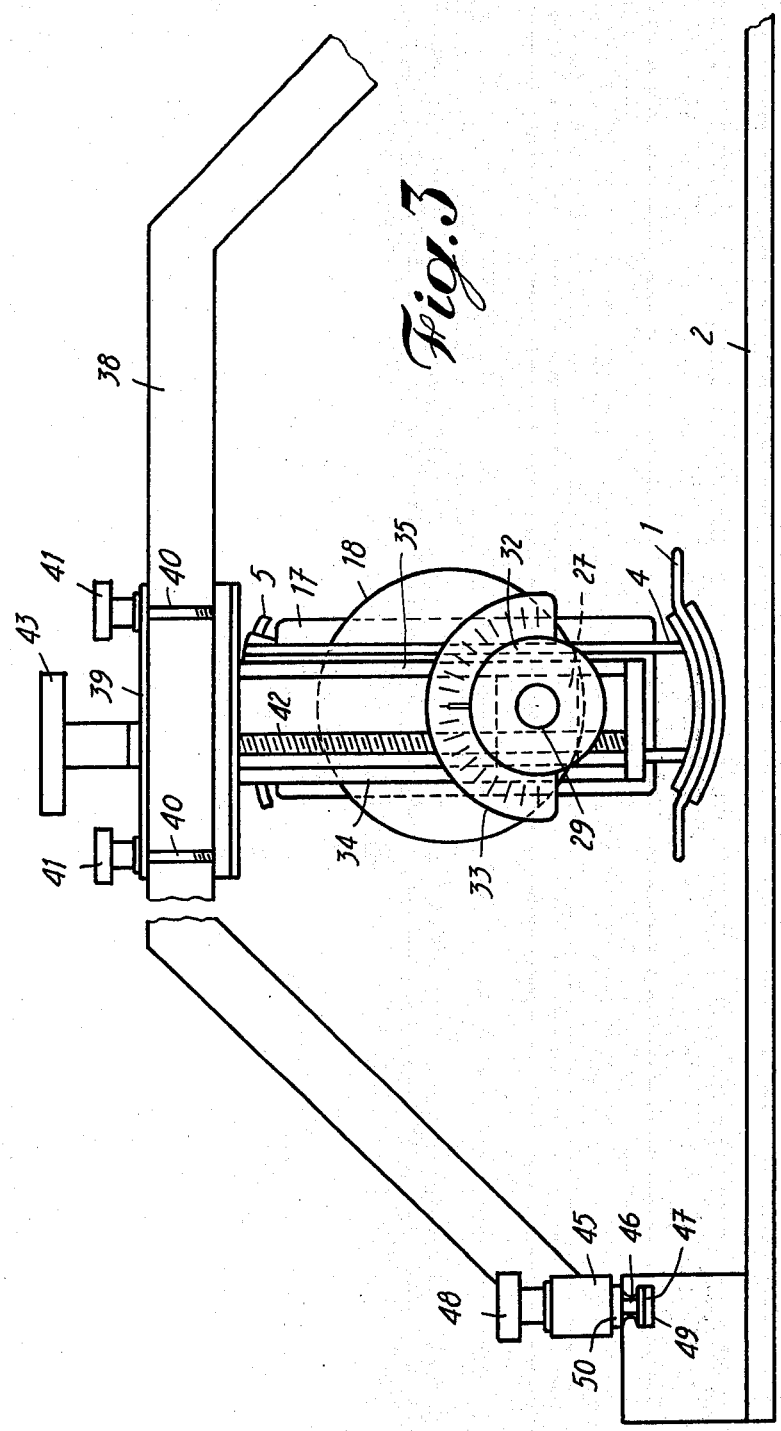
FIG. 3 shows a front view thereof.

In these figures carrier plate 1 can be noted, made out of any material which is permeable to X-rays and upon which may rest the to be radiographed skull of a person who lies stretched out upon the underlying bed 2 of the X-ray apparatus. Preferably this plate shall be slightly curved in transverse direction, so that the skull may easily rest within it. The rear edge of this plate is fixed by means of screws 3 to an upright linking element 4. At the top end of this linking element there is provided a slightly curved mobile plate 5 out of the same material as that of the carrier plate and which is hingedly attached by means of pivot 6. This plate is provided with a stop 7 which, in the horizontal position of the plate, rests against linking element 4. This plate is balanced in such a manner, that it remains in flapped-up position without the aid of complementary means. The distance between this upper plate 5 and the carrier plate 1 has been chosen in such a way that the plate can never touch the skull which rests upon the carrier plate. The width and length of upper plate 5 are considerably smaller than those of carrier plate 1. In the top plate a central longitudinal slot 8 is provided, whereas carrier plate 1 is provided towards each of its side edges with longitudinal slots respectively 9 and 10. Due to this arrangement, a strap 11 can be passed through slots 8 and 9 and tightened in such a manner, that skull A is maintained motionless between carrier plate 1 and strap 11, as shown in FIG. 4. Both extremities of the strap are secured upon the strap by means of adhesive strips 12 which are parts of the strap itself. In order to assure the most adequate fixing of the skull A, a further strap 13 provided with adhesive strips 14 may be passed through slots 10 of carrier plate 1 and tightened around the chin of the patient, as shown in FIG. 5. To the rear, at a small distance from linking element 4, an upright plate 17 is fixed upon an upper and a lower support, respectively 15 and 16, so that the crown of the skull may rest against it. Between linking element 4 and upright plate 17, a hand operated wheel 18 is fitted, the circumference of which is knurled. This handwheel is fixed upon a threaded bushing 19 which is free to rotate in a roller bearing 20, the latter being fitted into linking element 4. Screwed into threaded bushing 19 there is a pivot pin 21 provided with a transverse pin 22. This pin fits into a vertical slot 23 of a support 24, which together with a collar 25 are all parts of a shaft 26 which can rotate around its longitudinal axis and fits into the bearing of a slide 27, the height of which is adjustable. At its lower end, the support carries a pivot 28 upon which linking element 4 is hingedly fitted. When handwheel 18 is rotated, bushing 19 together with linking element 4 will be displaced by means of threaded pivot pin 21 in a direction which depends upon the sense of rotation of the handwheel. Linking element 4, and consequently also carrier plate 1, will then start to hinge around pivot 28, so that the carrier plate will take up the desired angular position which corresponds to the required position of the skull. By means of slot 23 and pin 22 which is engaged therein, pivot pin 21 can also follow the movement and place itself at an angle. The free end of shaft 26 is threaded and fitted with an end cap 29. To this same shaft a pointer 31 is fitted by means of a washer 30. The spacing between aforesaid washer 30 and end cap 29 is greater than the thickness of a locing knob 32 which is screwed upon shaft 26, so that this knob may be screwed loose on shaft 26 in order to permit the rotation of the latter around its center line and allow support 24, linking element 4 and consequently also carrier plate 1 to be adjusted transversally to the required angle. In order to fix carrier plate 1 in this position, it will be sufficient to tighten locking knob 32 upon shaft 26. The exact angle can then be read along the divisions of scale 33 which is fitted to slide 27. Locking knob 32 also makes it possible to clamp slide 27, which is adjustable in height, upon its two vertical guides 34 and 35. For this purpose the slide is provided with two ridges, respectively 36 and 37 which are pressed against guides 34,35 when the locking knob is tightened. Aforesaid guides 34, 35 are attached to a U-shaped sliding element 39 which can be displaced laterally across a bridge 38 and which can be clamped upon this bridge by means of two tightening rods 40 with knobs 41 which screw into the lower part of aforesaid sliding element 39. In order to be able to adjust the height of slide 27, use is made of a threaded rod 42 which screws into slide 27 and is fitted at its upper end with a handwheel 43. This rod is supported by a bearing in sliding element 39. In order to make possible the lateral displacement of this sliding element with rod 42 relative to aforesaid bridge, a longitudinal slot 44 has been provided in this bridge, through which slot rod 42 passes. Aforesaid bridge has been made sufficiently high to permit to slide measuring devices under it from the head side of the X-ray apparatus bed up to both sides of carrier plate 1. Both legs 45 of bridge 38 are each provided with a threaded tightening rod 46 which is attached on the one hand to a pull strip 47 and fitted on the other hand with a screw knob 48. The pulling strip fits into a longitudinal groove 49 in the bed 2 of the X-ray apparatus, and a washer 50 is provided between each foot and the bed, thus maintaining the entire device at a certain distance above the bed. In this manner bridge 38 can be displaced in the longitudinal sense of the bed and be clamped thereon by the mere tightening of knobs 48. To the rear foot is also provided with two screws 51 which attach strip 47 to the foot.

It is perfectly obvious that the dimensions, the shape and the relative position of the elements described above may differ and also that some of the parts described might be replaced by others which fulfill the same purpose. This skull clamp might also be completed with extra elements which might improve the practical operation thereof.

I claim:

1. Skull clamp, mainly for X-ray apparatus, comprising a carrier plate of a material which is permeable to X-ray and upon which rests the skull which has to be radiographed, means for strapping the skull to said carrier plate, a bridge above the bed of the X-ray apparatus and which can be displaced longitudinally with respect to aforesaid bed, means suspending said carrier plate from said bridge and capable of laterally displacing said carrier plate with respect to said bridge, means for adjusting the height of said carrier plate, means for adjusting in a transverse plane said carrier plate to an angle and means for adjusting in a longitudinal plane the position of said carrier plate to an angle.

2. Skull clamp as defined in claim 1, in which an upper plate is mounted above said carrier plate, at a distance which is greater than the thickness of the skull, an abutment plate against which the skull can rest, an element linking said carrier plate and said upper plate with said abutment plate, a strap being fitted between said upper plate and said carrier plate so as to be tightened against the temples of the patient, and a further strap being fitted to said carrier plate in order to be tightened over the chin of the patient.

3. Skull clamp as defined in claim 2, in which said upper plate is pivotally connected to said linking element for being pivoted upwards.

4. Skull clamp as defined in claim 2, in which at least one longitudinal slot is provided along each of the side edges of said carrier plate and one central longitudinal slot in said upper plate, the width of said upper plate being smaller than that of said carrier plate, said first strap passing through said slots in such a manner than when a pull is applied to the ends of said first strap, the skull is firmly held motionless between said carrier plate and said first strap.

5. Skull clamp as defined in claim 4 including adhesive strips on both extremities of said first strap whereby said extremities can be attached again first strap.

6. Skull clamp is defined in claim 1, in which said means for lateral displacement of said carrier plate consists of a sliding element mounted laterally and slideably on said bridge, means for fixing said sliding element on said bridge, and said carrier plate being suspended from said sliding element.

7. Skull clamp as defined in claim 1, in which the means for up and down displacement of said carrier plate consists of a slide with threaded bore and upon which said carrier plate is suspended, a threaded passing through said bore and having said slide thereon for being adjustable in height, a laterally mobile sliding element on the bridge and guides fixed to said sliding element and positioned for guiding said slide.

8. Skull clamp as defined in claim 2, in which said means for adjusting in a longitudinal plane said carrier plate to an angle consist of a horizontal shaft, a support fixed to said shaft and being provided at its upper end with vertical slot, a transverse pin in said vertical slot which is part of a threaded pivot pin, a handwheel screwable on said pivot pin and being coupled for free rotation to said linking element of said carrier plate, and said linking element also being hingedly attached to support.

* * * * *